US012681117B2

(12) United States Patent
Ma et al.

(10) Patent No.: US 12,681,117 B2
(45) Date of Patent: *Jul. 14, 2026

(54) SYSTEMS AND METHODS FOR INTEGRATED MAGNETIC RESONANCE IMAGING AND MAGNETIC RESONANCE FINGERPRINTING RADIOMICS ANALYSIS

(71) Applicant: Case Western Reserve University, Cleveland, OH (US)

(72) Inventors: Dan Ma, Solon, OH (US); Chaitra Badve, Moreland Hills, OH (US); Walter Zhao, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 1109 days.

This patent is subject to a terminal disclaimer.

(21) Appl. No.: 17/661,661

(22) Filed: May 2, 2022

(65) Prior Publication Data

US 2022/0349972 A1     Nov. 3, 2022

Related U.S. Application Data

(60) Provisional application No. 63/201,458, filed on Apr. 30, 2021.

(51) Int. Cl.
| | |
|---|---|
| *G01R 33/56* | (2006.01) |
| *A61B 5/055* | (2006.01) |
| *G16H 15/00* | (2018.01) |
| *G16H 30/40* | (2018.01) |

(52) U.S. Cl.
CPC .......... *G01R 33/5608* (2013.01); *A61B 5/055* (2013.01); *G01R 33/5601* (2013.01); *G16H 15/00* (2018.01); *G16H 30/40* (2018.01)

(58) Field of Classification Search
CPC ............ G01R 33/5608; G01R 33/5601; G01R 33/50; G01R 33/5602; G01R 33/5607; G01R 33/561; A61B 5/055; G16H 15/00; G16H 30/40; G16H 40/67
See application file for complete search history.

(56) References Cited

U.S. PATENT DOCUMENTS

| | | | |
|---|---|---|---|
| 2020/0050819 A1* | 2/2020 | Sommer | ............... G06T 7/0012 |
| 2020/0341092 A1* | 10/2020 | Jiang | ..................... G01R 33/50 |
| 2020/0341102 A1* | 10/2020 | Eck | .................... G01R 33/4828 |

OTHER PUBLICATIONS

Bipin Mehta, Bhairav, et al. "Magnetic resonance fingerprinting: a technical review." Magnetic resonance in medicine 31.1 (2019): 25-46.
Hoebel, Katharina V., et al. "Radiomics repeatability pitfalls in a scan-rescan MRI study of glioblastoma." Radiology: Artificial Intelligence 3.1 (2020): e190199.
Ma, Dan, et al. "Magnetic resonance fingerprinting." Nature 495. 7440 (2013): 187-192.

(Continued)

*Primary Examiner* — Lee E Rodak
*Assistant Examiner* — Zannatul Ferdous
(74) *Attorney, Agent, or Firm* — Quarles & Brady LLP

(57) ABSTRACT

Automated processing and radiomic analysis of magnetic resonance imaging ("MRI"), such as multi-contrast MR images, and magnetic resonance fingerprinting ("MRF") data, such as quantitative parameter maps, are integrated into a single workflow.

17 Claims, 5 Drawing Sheets

(56) References Cited

OTHER PUBLICATIONS

McGivney, Debra F., et al. "Magnetic resonance fingerprinting review part 2: Technique and directions." Journal of Magnetic Resonance Imaging 51.4 (2020): 993-1007.

MR Fingerprinting. Accessed Feb. 16, 2021. https://www.siemens-healthineers.com/magnetic-resonance-imaging/technologies-and-innovations/mr-fingerprinting.

Panda, Ananya, et al. "Magnetic resonance fingerprinting—an overview." Current opinion in biomedical engineering 3 (2017): 56-66.

Poorman, Megan E., et al. "Magnetic resonance fingerprinting Part 1: Potential uses, current challenges, and recommendations." Journal of Magnetic Resonance Imaging 51.3 (2020): 675-692.

* cited by examiner

SYSTEMS AND METHODS FOR INTEGRATED MAGNETIC RESONANCE IMAGING AND MAGNETIC RESONANCE FINGERPRINTING RADIOMICS ANALYSIS

CROSS-REFERENCE TO RELATED APPLICATIONS

This application claims the benefit of U.S. Provisional Patent Application Ser. No. 63/201,458, filed on Apr. 30, 2021, and entitled "SYSTEMS AND METHODS FOR INTEGRATED MAGNETIC RESONANCE IMAGING AND MAGNETIC RESONANCE FINGERPRINTING RADIOMICS ANALYSIS," which is herein incorporated by reference in its entirety.

STATEMENT REGARDING FEDERALLY SPONSORED RESEARCH

This invention was made with government support under EB026764 and NS109439 awarded by the National Institutes of Health. The government has certain rights in the invention.

BACKGROUND

Characterizing tissue species using nuclear magnetic resonance ("NMR") can include identifying different properties of a resonant species (e.g., T1 spin-lattice relaxation, T2 spin-spin relaxation, proton density). Other properties like tissue types and super-position of attributes can also be identified using NMR signals. These properties and others may be identified simultaneously using magnetic resonance fingerprinting ("MRF"), which is described, as one example, by D. Ma, et al., in "Magnetic Resonance Fingerprinting," Nature, 2013; 495(7440):187-192.

Conventional magnetic resonance imaging ("MRI") pulse sequences include repetitive similar preparation phases, waiting phases, and acquisition phases that serially produce signals from which images can be made. The preparation phase determines when a signal can be acquired and determines the properties of the acquired signal. For example, a first pulse sequence may produce a T1-weighted signal at a first echo time ("TE"), while a second pulse sequence may produce a T2-weighted signal at a second TE. These conventional pulse sequences typically provide qualitative results where data are acquired with various weightings or contrasts that highlight a particular parameter (e.g., T1 relaxation, T2 relaxation).

When magnetic resonance ("MR") images are generated, they may be viewed by a radiologist and/or surgeon who interprets the qualitative images for specific disease signatures. The radiologist may examine multiple image types (e.g., T1-weighted, T2-weighted) acquired in multiple imaging planes to make a diagnosis. The radiologist or other individual examining the qualitative images may need particular skill to be able to assess changes from session to session, from machine to machine, and from machine configuration to machine configuration.

Unlike conventional MRI, MRF employs a series of varied sequence blocks that simultaneously produce different signal evolutions in different resonant species (e.g., tissues) to which the radio frequency ("RF") is applied. The signals from different resonant tissues will, however, be different and can be distinguished using MRF. The different signals can be collected over a period of time to identify a signal evolution for the volume. Resonant species in the volume can then be characterized by comparing the signal evolution to known evolutions. Characterizing the resonant species may include identifying a material or tissue type, or may include identifying MR parameters associated with the resonant species. The "known" evolutions may be, for example, simulated evolutions calculated from physical principles and/or previously acquired evolutions. A large set of known evolutions may be stored in a dictionary.

MRF provides repeatable measurements of intrinsic tissue properties, offering improved diagnostic power over clinical qualitative MR imaging. However, there is currently no image processing platform that incorporates MRF analysis into the clinical workflow.

SUMMARY OF THE DISCLOSURE

The present disclosure addresses the aforementioned drawbacks by providing a method for generating radiomic feature data from magnetic resonance images and magnetic resonance fingerprinting maps. The method includes accessing with a computer system, magnetic resonance imaging (MRI) data acquired from a subject with an MRI system, and accessing with the computer system, magnetic resonance fingerprinting (MRF) data acquired from the subject, where the MRF data include quantitative parameter maps. The MRI data and the MRF data are preprocessed with the computer system, which may include coregistering the MRI data and the MRF data. An integrated radiomic analysis is performed on the preprocessed MRI data and the preprocessed MRF data, generating output as radiomic feature data. A report based on the radiomic feature data is generated with the computer system.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
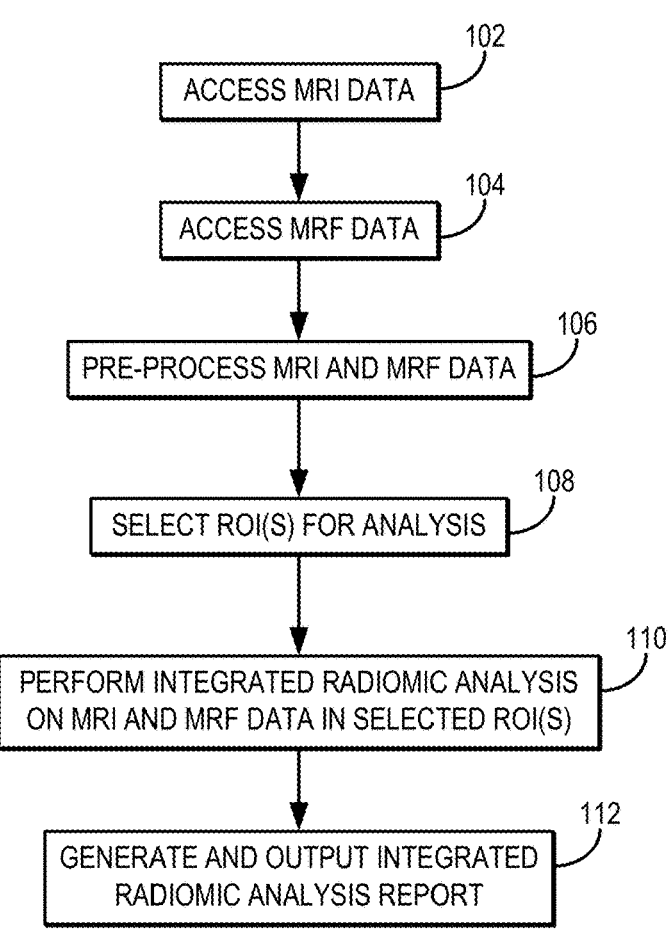
FIG. 1 is a flowchart setting forth the steps of an example method for performing integrated radiomic analysis on MRI and MRF data.

Described here are systems and methods for automated processing and radiomic analysis of magnetic resonance fingerprinting ("MRF") data, whether alone or in combination with other magnetic resonance imaging ("MRI") data, such as multi-contrast MRI data.

In an embodiment, following image reconstruction, MRF and MRI data are coregistered and may also be subjected to additional preprocessing. Quantitative analysis is performed on the coregistered images, which may include coregistered regions-of-interest ("ROIs"), and radiomic features can be derived therefrom. Statistical analyses of the radiomic feature data can additionally be performed. An image series with processed and coregistered MRF and MRI images is generated together with a report detailing the radiomic analysis of the image series. The systems and methods described in the present disclosure are flexible with respect to the specific MRF property maps and MRI contrasts used for processing and analysis.

Advantageously, the systems and methods described in the present disclosure improve upon existing MRI and MRF analysis techniques by reducing processing time through automation and increasing the reliability of radiomic information obtained from MRF images compared to MRI images. This latter advantage is because MRF data are quantitative property maps, unlike MRI data which is qualitative in nature and suffers from repeatability problems. The systems and methods described in the present disclosure also improve the ease of adoption of MRF technology by integrating and automating processing and analysis with conventional MRI. The analysis techniques are highly customizable regarding the use of individual MRF property maps and MRI contrasts.

MRF is a technique that facilitates mapping of tissue or other material properties based on random or pseudorandom measurements of the subject or object being imaged. In particular, MRF can be conceptualized as employing a series of varied "sequence blocks" that simultaneously produce different signal evolutions in different "resonant species" to which the RF is applied. The term "resonant species," as used herein, refers to a material, such as water, fat, bone, muscle, soft tissue, and the like, that can be made to resonate using NMR. By way of illustration, when radio frequency ("RF") energy is applied to a volume that has both bone and muscle tissue, then both the bone and muscle tissue will produce a nuclear magnetic resonance ("NMR") signal; however, the "bone signal" represents a first resonant species and the "muscle signal" represents a second resonant species, and thus the two signals will be different. These different signals from different species can be collected simultaneously over a period of time to collect an overall "signal evolution" for the volume.

The random or pseudorandom measurements obtained in MRF techniques are achieved by varying the acquisition parameters from one repetition time ("TR") period to the next, which creates a time series of signals with varying contrast. Examples of acquisition parameters that can be varied include flip angle ("FA"), RF pulse phase, TR, echo time ("TE'), and sampling patterns, such as by modifying one or more readout encoding gradients. The acquisition parameters are varied in a random manner, pseudorandom manner, or other manner that results in signals from different materials or tissues to be spatially incoherent, temporally incoherent, or both. For example, in some instances, the acquisition parameters can be varied according to a non-random or non-pseudorandom pattern that otherwise results in signals from different materials or tissues to be spatially incoherent, temporally incoherent, or both.

From these measurements, which as mentioned above may be random or pseudorandom, or may contain signals from different materials or tissues that are spatially incoherent, temporally incoherent, or both, MRF processes can be designed to map any of a wide variety of parameters. Examples of such parameters that can be mapped may include, but are not limited to, longitudinal relaxation time ("$T_1$"), transverse relaxation time ("$T_2$"), main or static magnetic field map ("$B_0$"), and proton density ("$\rho$"). MRF is generally described in U.S. Pat. Nos. 8,723,518 and 10,261,154, each of which is incorporated herein by reference in its entirety.

The data acquired with MRF techniques are compared with a dictionary of signal models, or templates, that have been generated for different acquisition parameters from magnetic resonance signal models, such as Bloch equation-based physics simulations. This comparison allows estimation of the physical parameters, such as those mentioned above. As an example, the comparison of the acquired signals to a dictionary can be performed using any suitable matching or pattern recognition technique. The parameters for the tissue or other material in a given voxel are estimated to be the values that provide the best signal template matching. For instance, the comparison of the acquired data with the dictionary can result in the selection of a signal vector, which may constitute a weighted combination of signal vectors, from the dictionary that best corresponds to the observed signal evolution. The selected signal vector includes values for multiple different quantitative parameters, which can be extracted from the selected signal vector and used to generate the relevant quantitative parameter maps.

The stored signals and information derived from reference signal evolutions may be associated with a potentially very large data space. The data space for signal evolutions can be partially described by:

$$SE = \sum_{s=1}^{N_S}\prod_{i=1}^{N_A}\sum_{j=1}^{N_{RF}} R_i(\beta)R_{RF_{ij}}(\alpha,\ \phi)R(G)E_i(T_1,\ T_2,\ D)M_0; \tag{1}$$

where SE is a signal evolution; $N_S$ is a number of spins; $N_A$ is a number of sequence blocks; $N_{RF}$ is a number of RF pulses in a sequence block; $\alpha$ is a flip angle; $\phi$ is a phase angle; $R_i(\beta)$ is a rotation due to off resonance, $\beta$; $R_{RF_{ij}}(\alpha,\phi)$ is a rotation due to RF differences; R(G) is a rotation due to a magnetic field gradient; $T_1$ is a longitudinal, or spin-lattice, relaxation time; $T_2$ is a transverse, or spin-spin, relaxation time; D is diffusion relaxation; $E_i(T_1,T_2,D)$ is a signal decay due to relaxation and diffusion; and $M_0$ is the magnetization in the default or natural alignment to which spins align when placed in the main magnetic field.

While $E_i(T_1,T_2,D)$ is provided as an example, in different situations, the decay term, $E_i(T_1,T_2,D)$, may also include additional terms, $E_i(T_1, T_2, D, \ldots)$ or may include fewer terms, such as by not including the diffusion relaxation, as $E_i(T_1, T_2)$ or $E_i(T_1, T_2, \ldots)$. Also, the summation on "j" could be replace by a product on "j".

The dictionary may store signals described by, $$S_i=R_iE_i(S_{i-1}) \tag{2};$$

where $S_0$ is the default, or equilibrium, magnetization; $S_i$ is a vector that represents the different components of magnetization, $M_x$, $M_y$, and $M_z$ during the $i^{th}$ acquisition block; $R_i$ is a combination of rotational effects that occur during the $i^{th}$ acquisition block; and $E_i$ is a combination of effects that alter the amount of magnetization in the different states for the $i^{th}$ acquisition block. In this situation, the signal at the $i^{th}$ acquisition block is a function of the previous signal at acquisition block (i.e., the $(i-1)^{th}$ acquisition block). Additionally or alternatively, the dictionary may store signals as a function of the current relaxation and rotation effects and of previous acquisitions. Additionally or alternatively, the dictionary may store signals such that voxels have multiple resonant species or spins, and the effects may be different for every spin within a voxel. Further still, the dictionary may store signals such that voxels may have multiple resonant species or spins, and the effects may be different for spins within a voxel, and thus the signal may be a function of the effects and the previous acquisition blocks.

As described above, data acquired with an MRF technique generally includes data containing random measurements, pseudorandom measurements, or measurements obtained in a manner that results in spatially incoherent signals, temporal incoherent signals, or spatiotemporally incoherent signals. For instance, such data can be acquired by varying acquisition parameters from one TR period to the next, which creates a time series of signals with varying contrast. Using this series of varied sequence blocks simultaneously produces different signal evolutions in different resonant species to which RF energy is applied.

As an example, data are acquired using a pulse sequence where effectuating the pulse sequence includes controlling an NMR apparatus (e.g., an MRI system) to apply RF energy to a volume in an object being imaged. The volume may contain one or more resonant species, such as tissue, fat, water, hydrogen, and prosthetics.

The RF energy may be applied in a series of variable sequence blocks. Sequence blocks may vary in a number of parameters including, but not limited to, echo time, flip angle, phase encoding, diffusion encoding, flow encoding, RF pulse amplitude, RF pulse phase, number of RF pulses, type of gradient applied between an excitation portion of a sequence block and a readout portion of a sequence block, number of gradients applied between an excitation portion of a sequence block and a readout portion of a sequence block, type of gradient applied between a readout portion of a sequence block and an excitation portion of a sequence block, number of gradients applied between a readout portion of a sequence block and an excitation portion of a sequence block, type of gradient applied during a readout portion of a sequence block, number of gradients applied during a readout portion of a sequence block, amount of RF spoiling, and amount of gradient spoiling. Depending upon the imaging or clinical need, two, three, four, or more parameters may vary between sequence blocks. The number of parameters varied between sequence blocks may itself vary. For example, a first sequence block may differ from a second sequence block in five parameters, the second sequence block may differ from a third sequence block in seven parameters, the third sequence block may differ from a fourth sequence block in two parameters, and so on. One skilled in the art will appreciate that there are a very-large number of series of sequence blocks that can be created by varying this large number of parameters. A series of sequence blocks can be crafted so that the series have different amounts (e.g., 1%, 2%, 5%, 10%, 50%, 99%, 100%) of unique sequence blocks as defined by their varied parameters. A series of sequence blocks may include more than ten, more than one hundred, more than one thousand, more than ten thousand, and more than one hundred thousand sequence blocks. In one example, the only difference between consecutive sequence blocks may be the number or parameters of excitation pulses.

Regardless of the particular imaging parameters that are varied or the number or type of sequence blocks, the RF energy applied during a sequence block is configured to cause different individual resonant species to simultaneously produce individual NMR signals. Unlike conventional imaging techniques, in an MRF pulse sequence, at least one member of the series of variable sequence blocks will differ from at least one other member of the series of variable sequence blocks in at least N sequence block parameters, where N is an integer greater than one. One skilled in the art will appreciate that the signal content of a signal evolution may vary directly with N. Thus, as more parameters are varied, a potentially richer signal is retrieved. Conventionally, a signal that depends on a single parameter is desired and required to facilitate imaging. Here, acquiring signals with greater information content facilitates producing more distinct, and thus more matchable, signal evolutions.

The pulse sequence used to acquire the provided data may apply members of the series of variable sequence blocks according to a partially random or pseudorandom acquisition plan configured to undersample the object at an undersampling rate, R. In different situations, the undersampling rate, R, may be, for example, two, four, or greater.

Unlike conventional MRI imaging processes, where the time during which an imaging-relevant NMR signal can be acquired is severely limited (e.g., 4-5 seconds), the NMR apparatus can be controlled to acquire NMR signal for significantly longer periods of time. For example, the NMR apparatus can be controlled to acquire signal for up to ten seconds, for up to twenty seconds, for up to one hundred seconds, or longer. NMR signals can be acquired for longer periods of time because signal information content remains viable for longer periods of time in response to the series of varied RF energy applied. In different situations, the information content in the signal evolution may remain above an information content threshold for at least five seconds, for at least ten seconds, for at least sixty seconds, or for longer. An information content threshold may describe, for example, the degree to which a subsequent signal acquisition includes information that can be retrieved and that differs from information acquired in a previous signal acquisition. For example, a signal that has no retrievable information would likely fall below an information content threshold while a signal with retrievable information that differs from information retrieved from a previous signal would likely be above the information content threshold.

Referring now to FIG. 1, a flowchart is illustrated as setting forth the steps of an example method for integrated processing and radiomic analysis of MRI and MRF data. The method includes accessing MRI data with a computer system, where the MRI data have been acquired from a subject using an MRI system, as indicated at step 102. Accessing the MRI data can include retrieving previously acquired MRI data from a memory or other suitable data storage media. Additionally or alternatively, accessing the MRI data can include acquiring the MRI data with an MRI system and transferring the MRI data from the MRI system to the computer system. In some instances, the MRI data can include multi-contrast MRI data. As an example, multi-contrast MRI data can include images of the subject with different contrast weightings. For instance, the multi-contrast MRI data can include two or more of T1-weighted images, contrast-enhanced T1-weighted images, T2-weighted images, fluid attenuation inversion recovery ("FLAIR") images, proton density-weighted images, diffusion-weighted images, and susceptibility-weighted images.

The method also includes accessing MRF data with a computer system, as indicated at step 104. Accessing the MRF data can include retrieving previously generated MRF data from a memory or other suitable data storage media. Additionally or alternatively, accessing the MRF data can include acquiring magnetic resonance data with an MRI system, generating MRF data therefrom, and transferring the MRF data to the computer system. As an example, the MRF data can include quantitative parameter maps, such as $M_0$ maps, T1 maps, T2 maps, diffusion parameter maps, perfusion parameter maps, and so on. For instance, the quantitative parameter maps can be generated using MRF data acquisition and dictionary matching techniques, such as those described above.

The MRI data and the MRF data can then be preprocessed by the computer system, as indicated at step 106. For instance, preprocessing the MRI and/or MRF data can include denoising, bias corrections, skull stripping (in the case of brain imaging), intensity normalization, and so on. As an example, raw multi-contrast MRI images can undergo preprocessing steps including but not limited to file conversion, denoising, and bias correction. MRF and MRI images can then undergo combined preprocessing including but not limited to skull stripping and coregistration. The MRI images can then undergo additional processing steps including but not limited to intensity normalization.

One or more ROIs are then selected for analysis, as indicated at step 108. ROIs can be obtained from the MRI data, the MRF data, or both. As a non-limiting example, ROIs can be obtained from parameter maps contained in the MRF data. The ROI(a) can be manually, semi-automatically, or automatically selected. As one example, the ROI(s) can be manually selected by a clinician or other user, such as by identifying pixels and/or spatial locations within the MRI and/or MRF data that are to be included in the one or more ROIs. As another example, the ROIs can be selected semi-automatically or automatically. For instance, an image segmentation algorithm or the like can be implemented using a computer system to select one or more ROIs in the MRI data and/or MRF data. The selected ROI(s) can optionally be presented to a user for refinement (e.g., refining the boundaries of a selected ROI). In some instances, the segmentation algorithm may be implemented using artificial intelligence or other machine learning techniques. For example, a neural network, such as a convolutional neural network, can be trained on suitable training data to receive input data as a MRI data and/or MRF data and to generate output data as MRI data and/or MRF data that have been segmented to identify one or more ROIs.

Statistical or other quantitative analyses are then performed using the ROIs obtained from the MRI data and/or MRF data, as indicated at step 110. If obtained from the MRI data, the ROIs are coregistered to MRF images prior to analysis. The statistical or other quantitative analyses can include radiomic analysis.

As a non-limiting example, radiomic analysis can include extracting radiomic features from the MRI and/or MRF data in the selected ROIs and storing the extracted features as radiomic feature data. Radiomic features can include shape features (e.g., volume, surface area of the selected ROIs), first-order statistical features (e.g., mean, variance), second-order statistical features, or combinations thereof.

In general, second-order statistics are computed from a probability function that measures the probability of a pair of pixel values occurring at some offset in an image. This probability function is typically referred to as a "co-occurrence matrix" because it measures the probability of two pixel values co-occurring at the given offset. An example of the co-occurrence matrix is the gray-level co-occurrence matrix ("GLCM"). Another matrix that can be used to compute second-order statistics is the gray-level run length matrix ("GLRLM"). Still other matrices that can be used to compute second-order statistics is the gray-level size zone matrix ("GLSZM"), the neighborhood gray tone difference matrix ("NGTDM"), the gray level dependence matrix ("GLDM"), and so on. Second-order statistics can generally be referred to as textural features of an image.

The GLCM represents, statistically, the angular relationship between neighboring pixels as well as the distance between them. Based on the statistical information provided by a GLCM, several textural features can be defined and extracted. By way of example, the second-order statistical features may include contrast, energy, homogeneity, correlation, autocorrelation, dissimilarity, GLCM variance, entropy, cluster shade, cluster prominence, maximum probability, or other suitable second-order statistical measures. Contrast ("CON") represents a measure of difference between the lowest and highest intensities in a set of pixels. Energy ("ENE") measures the frequency of occurrence of pixel pairs and quantifies its power as the square of the frequency of gray-level transitions. Homogeneity ("HOM") measures the incidence of pixel pairs of different intensities; thus, as the frequency of pixel pairs with close intensities increases, HOM increases. Correlation ("COR") measures the intensity correlation between pixel pairs.

The GLRLM represents, run length metrics that can quantify gray level runs in an image. In general, a gray level run is the length, in number of pixels, of consecutive pixels that have the same gray level value. In a gray level run length matrix, $P(i,j|\theta)$, the element $(i,j)$ describes the number of runs with gray level, i, and run length, j, that occur in the image, or analyzed region within the image, along the angle, $\theta$. By way of example, the second-order statistical features determined from a GLRLM may include short run emphasis, long run emphasis, gray-level nonuniformity, run-length nonuniformity, run percentage, low gray-level run emphasis, high gray-level run emphasis, short run low gray-level emphasis, short run high gray-level emphasis, long run low gray-level emphasis, long run high gray-level emphasis, gray-level variance, run-length variance, and so on.

The GLSZM represents the amount of homogeneous connected areas of a certain size and/or intensity within a region of an image. Each entry $(i,j)$ in the GLSZM is the number of connected areas of gray level, i, and size, j. Features extracted from the GLSZM thus describe homogeneous areas within the tumor regions, which can provide information about tumor heterogeneity at a regional scale. By way of example, the second-order statistical features determined from a GLSZM may include small zone emphasis, large zone emphasis, gray-level nonuniformity, zone-size nonuniformity, zone percentage, low gray-level zone emphasis, high gray-level zone emphasis, small zone low gray-level zone emphasis, small zone high gray-level zone emphasis, large zone low gray-level zone emphasis, large zone high gray-level zone emphasis, gray-level variance, zone-size variance, and so on.

The NGTDM quantifies the difference between a gray value and the average gray value of its neighbors within distance, $\delta$. Each entry, $(i|\delta)$, of the NGTDM is the sum of gray level differences of voxels with intensity (i.e., gray level), i, and the average intensity, $A_i$, of their neighboring voxels within a distance, $\delta$. By way of example, the second-order statistical features determined from a NGTDM may include coarseness, contrast, busyness, complexity, strength, and so on.

The GLDM quantifies gray level dependencies in an image. A gray level dependency can be defined as a the number of connected voxels within distance, $\delta$, that are dependent on a center voxel. A neighboring voxel with gray level, j, is considered dependent on a center voxel with gray level, i, when $|i-j| \leq \alpha$ for some parameter, $\alpha$. Thus, in the GLDM each entry, (i,j), describes the number of times a voxel with gray level, i, with j dependent voxels in its neighborhood appears in image. By way of example, the second-order statistical features determined from a GLDM may include small dependence emphasis, large dependence emphasis, gray level nonuniformity, dependence nonuniformity, gray-level variance, dependence variance, dependence entropy, low gray-level emphasis, high gray-level emphasis, small dependence low gray-level emphasis, small dependence high gray-level emphasis, large dependence low gray-level emphasis, large dependence high gray-level emphasis, and so on.

In some embodiments, to estimate second-order statistical measures the images and/or parametric maps in the MRI and/or MRF data are processed using a GLCM-based texture analysis process to extract the aforementioned second-order statistical measures, which may also be referred to as textural features. A GLCM is an $N_g \times N_g$ matrix, where $N_g$ is the number of quantized gray levels in the image for which the GLCM is computed (e.g., the parametric maps in this instance). Each element in the GLCM, p(i,j), is a statistical probability value for changes between the $i^{th}$ and $j^{th}$ gray levels at a particular displacement distance, d, and angle, $\theta$. Thus, given p(i,j) as an element in an $N_g \times N_g$ GLCM, the above-mentioned textural parameters can be defined as follows:

$$CON = \sum_{k=0}^{N_g-1} k^2 \left( \sum_{i=1}^{N_g} \sum_{j=1}^{N_g} p(i,j) \right) \text{ with } k = |i-j|; \quad (3)$$

$$ENE = \sum_{i=1}^{N_g} \sum_{j=1}^{N_g} p(i,j)^2; \quad (4)$$

$$HOM = \sum_{i=1}^{N_g} \sum_{j=1}^{N_g} \frac{p(i,j)}{1+|i-j|}; \quad (5)$$

$$COR = \frac{\sum_{i=1}^{N_g} \sum_{j=1}^{N_g} (i-\mu_x)(j-\mu_y)p(i,j)}{\sigma_x \sigma_y}; \quad (6)$$

where $\mu_x$ and $\mu_y$ are the means for the columns and rows, respectively, of the GLCM, $$\mu_x = \sum_{i=1}^{N_g} \sum_{j=1}^{N_g} i \cdot p(i,j); \quad (7)$$

$$\mu_y = \sum_{i=1}^{N_g} \sum_{j=1}^{N_g} j \cdot p(i,j); \quad (8)$$

and where $\sigma_x$ and $\sigma_y$ are the standard deviations for the columns and rows, respectively, of the GLCM, $$\sigma_x^2 = \sum_{i=1}^{N_g} \sum_{j=1}^{N_g} (i-\mu_x)^2 \cdot p(i,j); \quad (9)$$

-continued
$$\sigma_y^2 = \sum_{i=1}^{N_g} \sum_{j=1}^{N_g} (j-\mu_y)^2 \cdot p(i,j). \quad (10)$$

A number of different GLCMs can be constructed for each image or parametric map in the MRI and/or MRF data. For example, sixteen symmetric GLCMs can be constructed considering each pixel's neighbors located at the displacement distances, d, of one to four pixels with angular values, $\theta$, of 0-135 degrees with 45 degree increments. The second-order statistical measures, or textural features, can then be extracted from the corresponding GLCMs of each image or parametric map in the MRI and/or MRF data and stored as the radiomic feature data. In some instances, regions within the MRI and/or MRF data can be separately processed to compute radiomic feature data for those regions (e.g., by processing the pixels in the identified ROIs).

Referring still to FIG. 1, a report is then generated describing the results extracted from each image, as indicated at step 112. The report may include images, parameter maps, feature maps, visual depictions of parameters and/or measurements computed from such images or maps, other related information, and combinations thereof.

In an example study, multi-contrast MRI data were obtained and included T1-weighted images, contrast-enhanced T1-weighted images, T2-weighted images, FLAIR images, diffusion images, and susceptibility-weighted images. The images were denoised and bias corrected. MR images and MRF-derived $M_0$, T1, and T2 quantitative maps were then skull stripped following tissue class segmentation. Specifically, T2-weighted and $M_0$ map brain masks were generated. The other MR images were affinely registered to the T2-weighted images using a maximization of normalized mutual information ("NMI") approach and were skull stripped using the T2-weighted brain mask. MRF maps were skull stripped using the $M_0$ brain mask.

Figure 2:
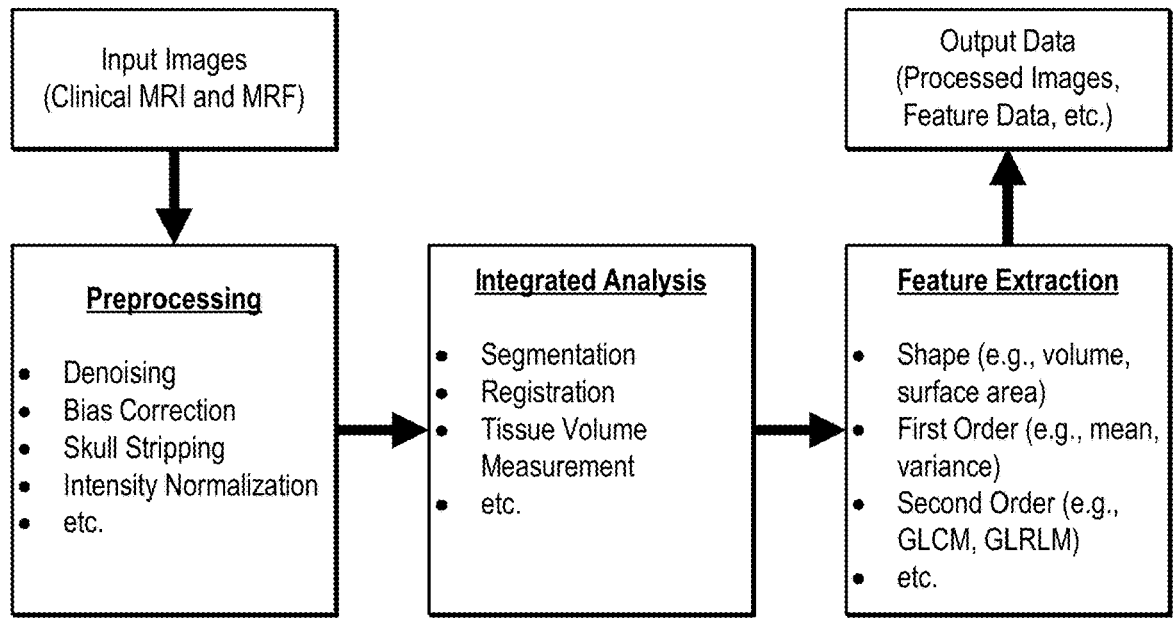
FIG. 2 shows an example workflow for an example integrated radiomic analysis according to an embodiment described in the present disclosure.

The MR images were then affinely registered to the MRF maps with the T1 map as a reference image using an NMI similarity measure. The MR images were also z-score normalized. Because the MRF maps provide quantitative measurements, preprocessing such as bias correction and intensity normalization were not performed on the MRF data. The MRF maps were also selected as reference during registration to retain original voxel values. Feature extraction was then performed on coregistered images using ROIs obtained from the MRF maps via the Cancer Imaging Phenomics Toolkit. An example workflow for integrated clinical MRI and MRF processing and analysis is shown in FIG. 2.

MRI studies featuring T1-weighted, contrast-enhanced T1-weighted images, T2-weighted images, FLAIR images, diffusion images, and susceptibility-weighted images were analyzed in tandem with MRF-derived M0, T1, and T2 maps. ROIs of enhancing solid tumor and peritumoral white matter ("PW") were generated from automatic segmentation on MRF maps according to T2 hyperintensity, with the PW region being further segmented into near and far regions.

Figure 3:
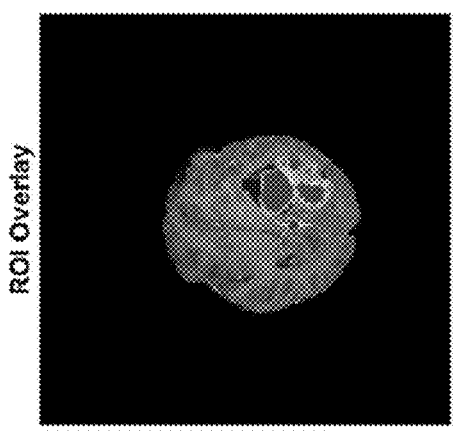
FIG. 3 is an example output of the processing workflow for a contrast-enhanced T1-weighted image (top) and a corresponding T1 map (bottom) with ROI overlay, which are ready for combined analysis.
Figure 3:
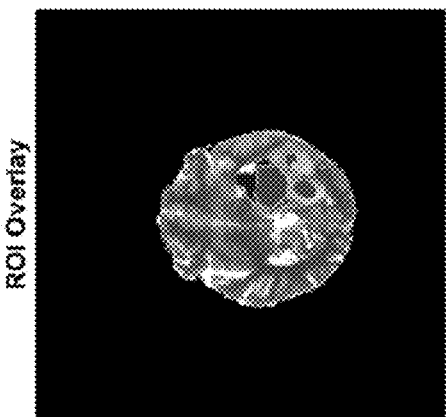
Figure 3:
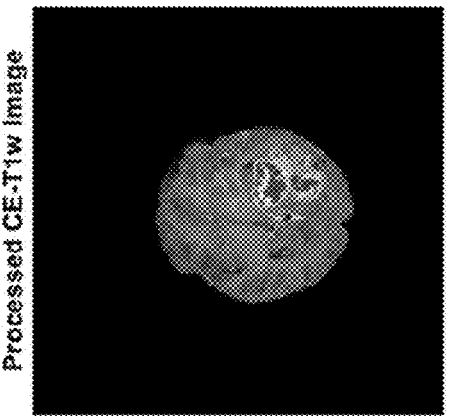
Figure 3:
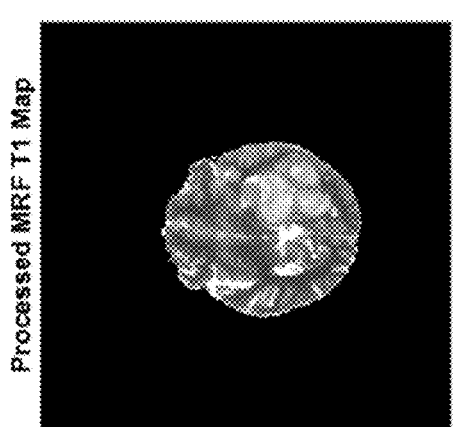
Figure 3:
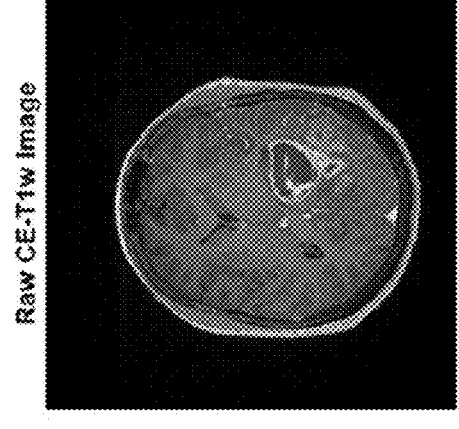
Figure 3:
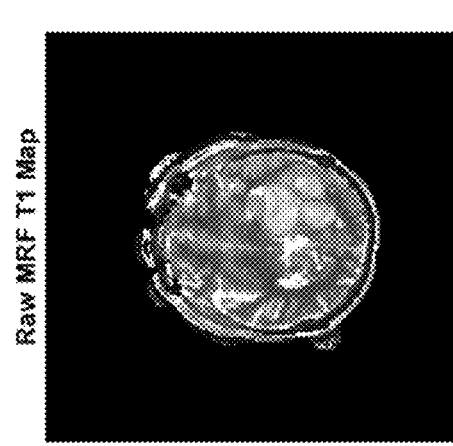

FIG. 3 shows the results of an example processing workflow for a contrast-enhanced T1-weighted image (top) and corresponding MRF-derived T1 map (bottom) with ROI overlay. Using the example workflow described above, the MRF maps can be analyzed alongside clinical MR images. Several types of features can be extracted, including shape features (e.g., volume and surface area), first-order statistical features (e.g., mean and variance of image values within the ROIs), and second-order statistical features (e.g., GLCM- and/or GLRLM-based features).

Execution of the complete workflow produces an MRI series containing qualitative clinical MR images and quantitative MRF maps that have been preprocessed for downstream analysis. Workflow performance shows advantageous reproducibility for structural modalities. Feature extraction for evaluating tumor regions is also enabled. As an advantageous example, non-overlapping differences can be observed in various peritumoral regions in radiomic features derived from structural, diffusion, and MRF data. It is therefore contemplated that MRF can provide unique information in tissue characterization that is complementary to commonly used radiomic data and may be used to enrich radiomic analysis.

Referring particularly now to FIG. 3, an example of an MRI system 300 that can implement the methods described here is illustrated. The MRI system 300 includes an operator workstation 302 that may include a display 304, one or more input devices 306 (e.g., a keyboard, a mouse), and a processor 308. The processor 308 may include a commercially available programmable machine running a commercially available operating system. The operator workstation 302 provides an operator interface that facilitates entering scan parameters into the MRI system 300. The operator workstation 302 may be coupled to different servers, including, for example, a pulse sequence server 310, a data acquisition server 312, a data processing server 314, and a data store server 316. The operator workstation 302 and the servers 310, 312, 314, and 316 may be connected via a communication system 340, which may include wired or wireless network connections.

The pulse sequence server 310 functions in response to instructions provided by the operator workstation 302 to operate a gradient system 318 and a radiofrequency ("RF") system 320. Gradient waveforms for performing a prescribed scan are produced and applied to the gradient system 318, which then excites gradient coils in an assembly 322 to produce the magnetic field gradients $G_x$, $G_y$, and $G_z$ that are used for spatially encoding magnetic resonance signals. The gradient coil assembly 322 forms part of a magnet assembly 324 that includes a polarizing magnet 326 and a whole-body RF coil 328.

RF waveforms are applied by the RF system 320 to the RF coil 328, or a separate local coil to perform the prescribed magnetic resonance pulse sequence. Responsive magnetic resonance signals detected by the RF coil 328, or a separate local coil, are received by the RF system 320. The responsive magnetic resonance signals may be amplified, demodulated, filtered, and digitized under direction of commands produced by the pulse sequence server 310. The RF system 320 includes an RF transmitter for producing a wide variety of RF pulses used in MRI pulse sequences. The RF transmitter is responsive to the prescribed scan and direction from the pulse sequence server 310 to produce RF pulses of the desired frequency, phase, and pulse amplitude waveform. The generated RF pulses may be applied to the whole-body RF coil 328 or to one or more local coils or coil arrays.

The RF system 320 also includes one or more RF receiver channels. An RF receiver channel includes an RF preamplifier that amplifies the magnetic resonance signal received by the coil 328 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \tag{11};$$

and the phase of the received magnetic resonance signal may also be determined according to the following relationship:

$$\varphi = \tan^{-1}\left(\frac{Q}{I}\right). \tag{12}$$

The pulse sequence server 310 may receive patient data from a physiological acquisition controller 330. By way of example, the physiological acquisition controller 330 may receive signals from a number of different sensors connected to the patient, including electrocardiograph ("ECG") signals from electrodes, or respiratory signals from a respiratory bellows or other respiratory monitoring devices. These signals may be used by the pulse sequence server 310 to synchronize, or "gate," the performance of the scan with the subject's heart beat or respiration.

The pulse sequence server 310 may also connect to a scan room interface circuit 332 that receives signals from various sensors associated with the condition of the patient and the magnet system. Through the scan room interface circuit 332, a patient positioning system 334 can receive commands to move the patient to desired positions during the scan.

The digitized magnetic resonance signal samples produced by the RF system 320 are received by the data acquisition server 312. The data acquisition server 312 operates in response to instructions downloaded from the operator workstation 302 to receive the real-time magnetic resonance data and provide buffer storage, so that data is not lost by data overrun. In some scans, the data acquisition server 312 passes the acquired magnetic resonance data to the data processor server 314. In scans that require information derived from acquired magnetic resonance data to control the further performance of the scan, the data acquisition server 312 may be programmed to produce such information and convey it to the pulse sequence server 310. For example, during pre-scans, magnetic resonance data may be acquired and used to calibrate the pulse sequence performed by the pulse sequence server 310. As another example, navigator signals may be acquired and used to adjust the operating parameters of the RF system 320 or the gradient system 318, or to control the view order in which k-space is sampled. In still another example, the data acquisition server 312 may also process magnetic resonance signals used to detect the arrival of a contrast agent in a magnetic resonance angiography ("MRA") scan. For example, the data acquisition server 312 may acquire magnetic resonance data and processes it in real-time to produce information that is used to control the scan.

The data processing server 314 receives magnetic resonance data from the data acquisition server 312 and processes the magnetic resonance data in accordance with instructions provided by the operator workstation 302. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 314 are conveyed back to the operator workstation 302 for storage. Real-time images may be stored in a data base memory cache, from which they may be output to operator display 302 or a display 336. Batch mode images or selected real time images may be stored in a host database on disc storage 338. When such images have been reconstructed and transferred to storage, the data processing server 314 may notify the data store server 316 on the operator workstation 302. The operator workstation 302 may be used by an operator to archive the images, produce films, or send the images via a network to other facilities.

The MRI system 300 may also include one or more networked workstations 342. For example, a networked workstation 342 may include a display 344, one or more input devices 346 (e.g., a keyboard, a mouse), and a processor 348. The networked workstation 342 may be located within the same facility as the operator workstation 302, or in a different facility, such as a different healthcare institution or clinic.

The networked workstation 342 may gain remote access to the data processing server 314 or data store server 316 via the communication system 340. Accordingly, multiple networked workstations 342 may have access to the data processing server 314 and the data store server 316. In this manner, magnetic resonance data, reconstructed images, or other data may be exchanged between the data processing server 314 or the data store server 316 and the networked workstations 342, such that the data or images may be remotely processed by a networked workstation 342.

Figure 4:
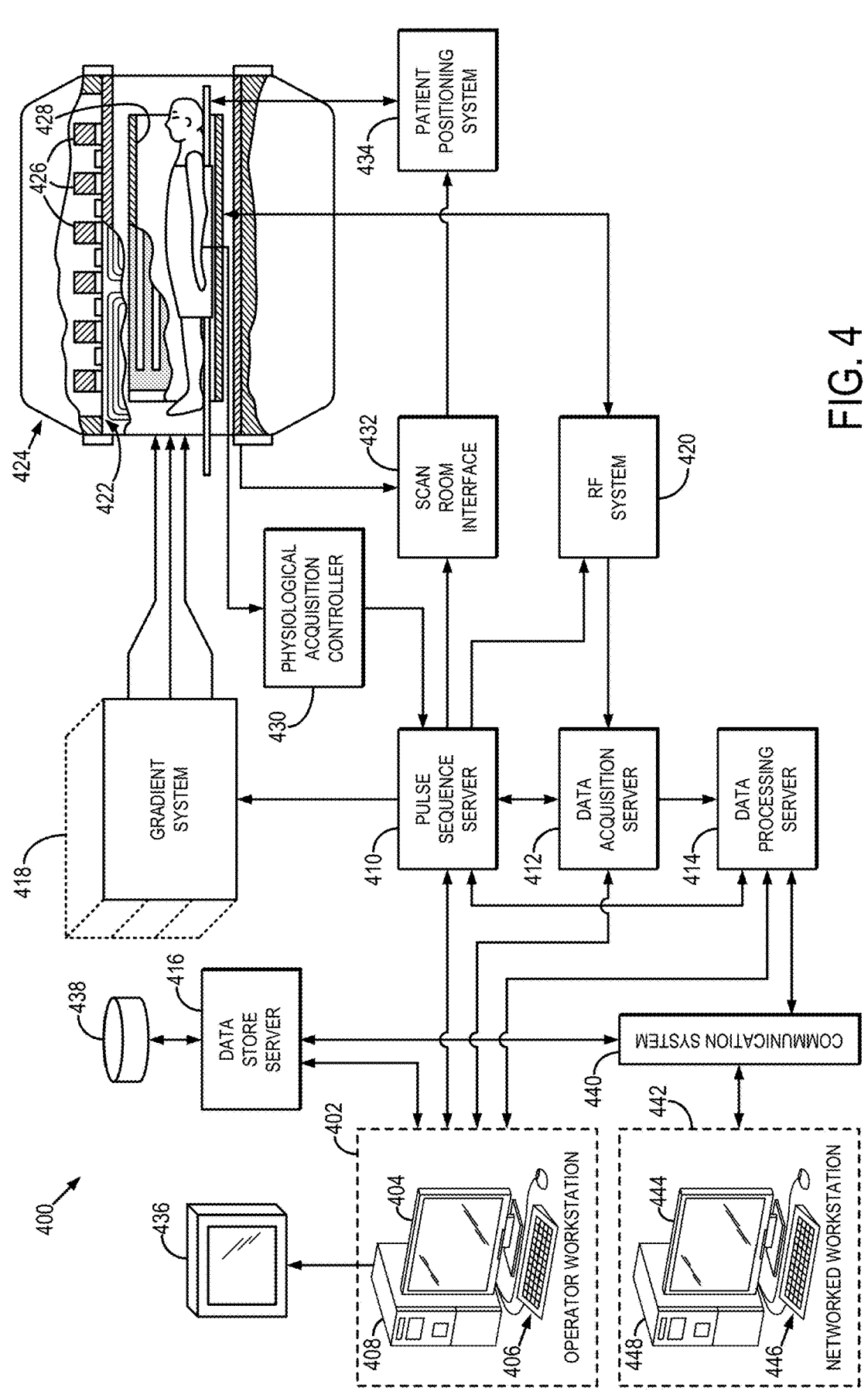
FIG. 4 is a block diagram of an example MRI system that can be implemented in some embodiments described in the present disclosure.

Referring now to FIG. 4, an example of a system 400 for integrated MRI and MRF radiomics analysis in accordance with some embodiments of the systems and methods described in the present disclosure is shown. As shown in FIG. 4, a computing device 450 can receive one or more types of data (e.g., MRI data, MRF data) from data source 402, which may be an MRI data source. In some embodiments, computing device 450 can execute at least a portion of an integrated MRI and MRF radiomics analysis system 404 to perform radiomic analysis from MRI and MRF data received from the data source 402.

Additionally or alternatively, in some embodiments, the computing device 450 can communicate information about data received from the data source 402 to a server 452 over a communication network 454, which can execute at least a portion of the integrated MRI and MRF radiomics analysis system 404. In such embodiments, the server 452 can return information to the computing device 450 (and/or any other suitable computing device) indicative of an output of the integrated MRI and MRF radiomics analysis system 404.

In some embodiments, computing device 450 and/or server 452 can be any suitable computing device or combination of devices, such as a desktop computer, a laptop computer, a smartphone, a tablet computer, a wearable computer, a server computer, a virtual machine being executed by a physical computing device, and so on. The computing device 450 and/or server 452 can also reconstruct images from the data.

In some embodiments, data source 402 can be any suitable source of image data (e.g., measurement data, images reconstructed from measurement data), such as an MRI system, another computing device (e.g., a server storing image data), and so on. In some embodiments, data source 402 can be local to computing device 450. For example, data source 402 can be incorporated with computing device 450 (e.g., computing device 450 can be configured as part of a device for capturing, scanning, and/or storing images). As another example, data source 402 can be connected to computing device 450 by a cable, a direct wireless link, and so on. Additionally or alternatively, in some embodiments, data source 402 can be located locally and/or remotely from computing device 450, and can communicate data to computing device 450 (and/or server 452) via a communication network (e.g., communication network 454).

In some embodiments, communication network 454 can be any suitable communication network or combination of communication networks. For example, communication network 454 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 4 can each be any suitable communications link or combination of communications links, such as wired links, fiber optic links, Wi-Fi links, Bluetooth links, cellular links, and so on.

Figure 5:
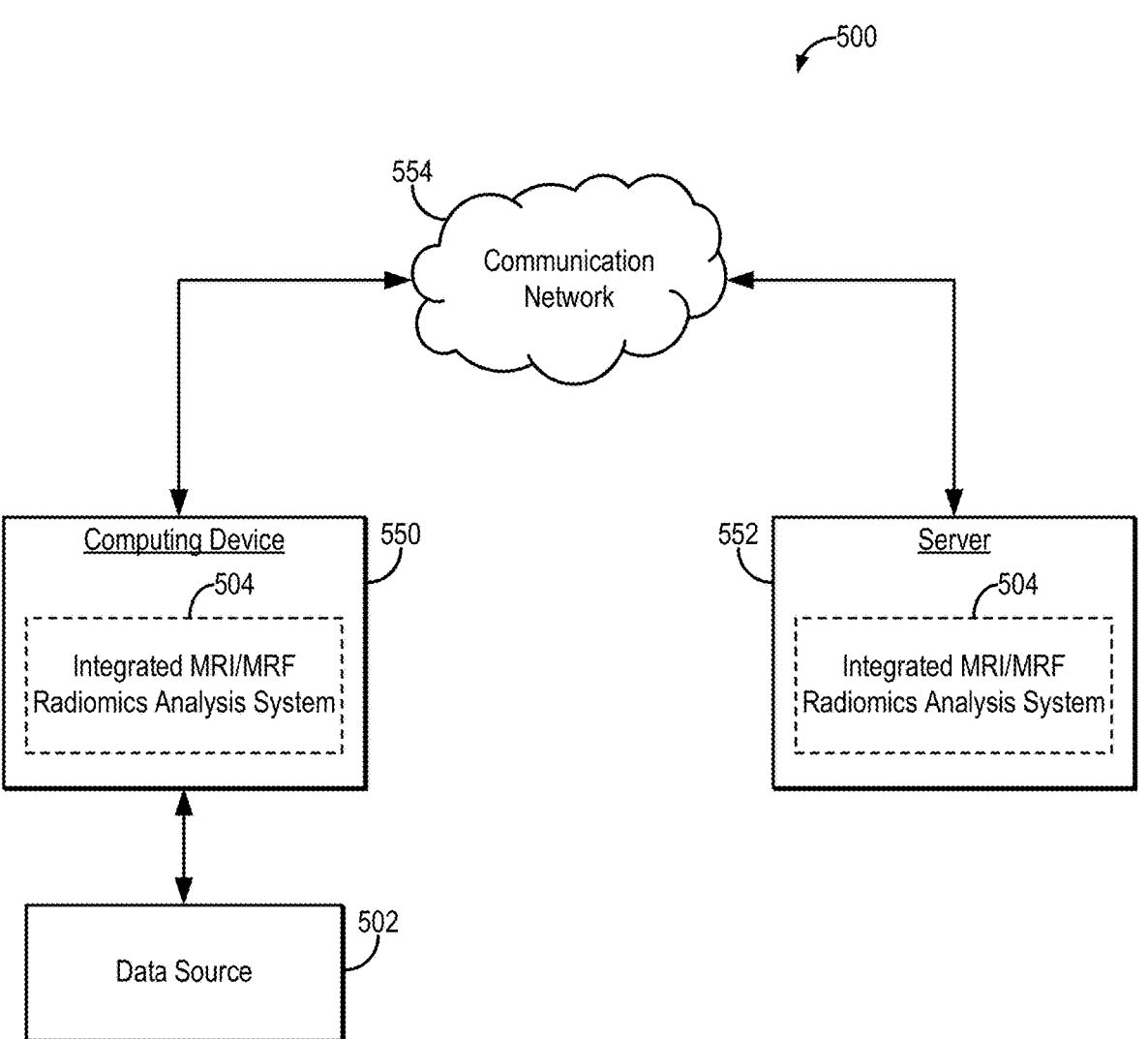
FIG. 5 is a block diagram of an example integrated MRI/MRF radiomics analysis system.
Figure 6:
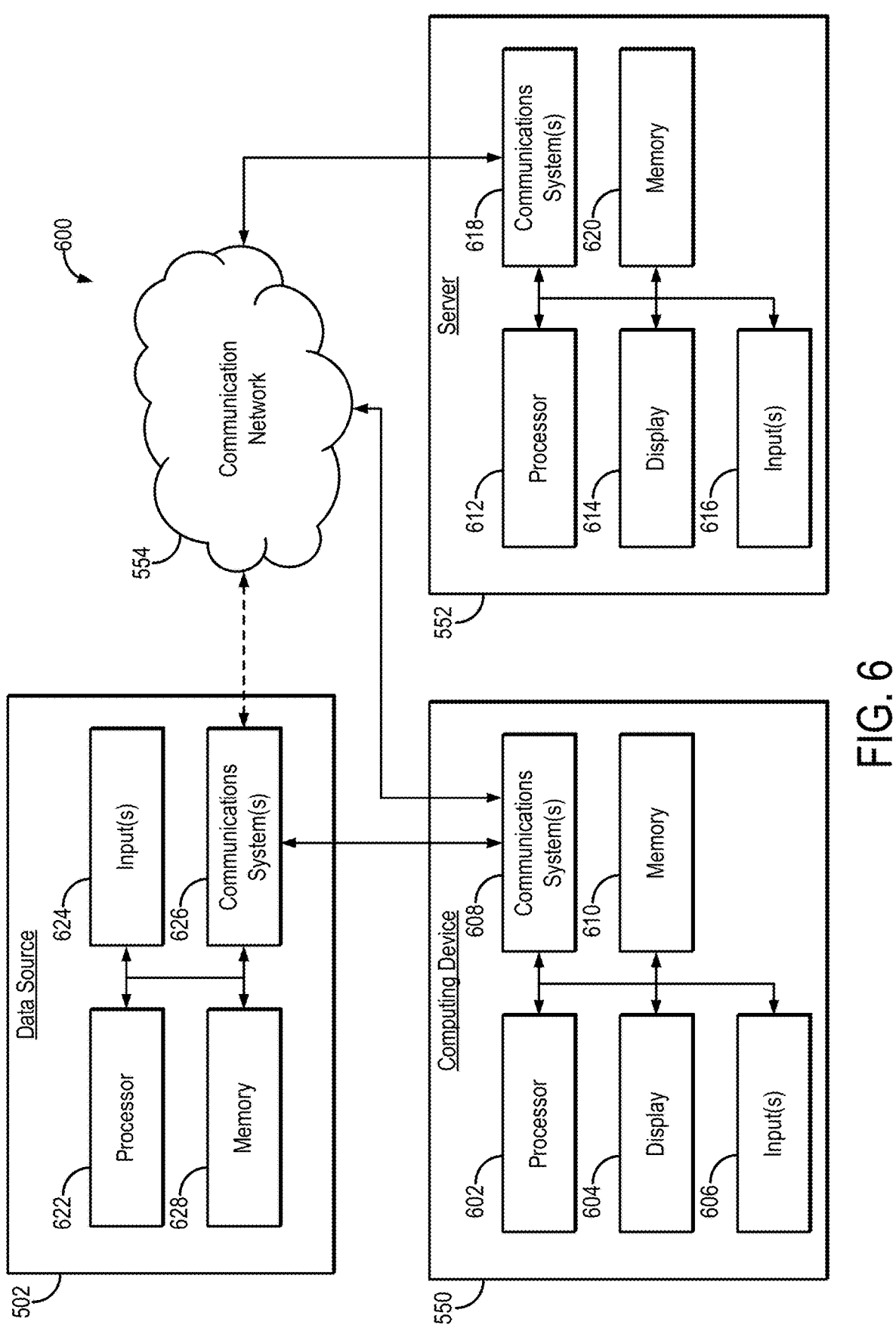
FIG. 6 is a block diagram of example components that can implement the system of FIG. 5.

Referring now to FIG. 5, an example of hardware 500 that can be used to implement data source 402, computing device 450, and server 454 in accordance with some embodiments of the systems and methods described in the present disclosure is shown. As shown in FIG. 5, in some embodiments, computing device 450 can include a processor 502, a display 504, one or more inputs 506, one or more communication systems 508, and/or memory 510. In some embodiments, processor 502 can be any suitable hardware processor or combination of processors, such as a central processing unit ("CPU"), a graphics processing unit ("GPU"), and so on. In some embodiments, display 504 can include any suitable display devices, such as a computer monitor, a touchscreen, a television, and so on. In some embodiments, inputs 506 can include any suitable input devices and/or sensors that can be used to receive user input, such as a keyboard, a mouse, a touchscreen, a microphone, and so on.

In some embodiments, communications systems 508 can include any suitable hardware, firmware, and/or software for communicating information over communication network 454 and/or any other suitable communication networks. For example, communications systems 508 can include one or more transceivers, one or more communication chips and/or chip sets, and so on. In a more particular example, communications systems 508 can include hardware, firmware and/or software that can be used to establish a Wi-Fi connection, a Bluetooth connection, a cellular connection, an Ethernet connection, and so on.

In some embodiments, memory 510 can include any suitable storage device or devices that can be used to store instructions, values, data, or the like, that can be used, for example, by processor 502 to present content using display 504, to communicate with server 452 via communications system(s) 508, and so on. Memory 510 can include any suitable volatile memory, non-volatile memory, storage, or any suitable combination thereof. For example, memory 510 can include RAM, ROM, EEPROM, one or more flash drives, one or more hard disks, one or more solid state drives, one or more optical drives, and so on. In some embodiments, memory 510 can have encoded thereon, or otherwise stored therein, a computer program for controlling operation of computing device 450. In such embodiments, processor 502 can execute at least a portion of the computer program to present content (e.g., images, user interfaces, graphics, tables), receive content from server 452, transmit information to server 452, and so on.

In some embodiments, server 452 can include a processor 512, a display 514, one or more inputs 516, one or more communications systems 518, and/or memory 520. In some embodiments, processor 512 can be any suitable hardware processor or combination of processors, such as a CPU, a GPU, and so on. In some embodiments, display 514 can include any suitable display devices, such as a computer monitor, a touchscreen, a television, and so on. In some embodiments, inputs 516 can include any suitable input devices and/or sensors that can be used to receive user input, such as a keyboard, a mouse, a touchscreen, a microphone, and so on.

In some embodiments, communications systems 518 can include any suitable hardware, firmware, and/or software for communicating information over communication network 454 and/or any other suitable communication networks. For example, communications systems 518 can include one or more transceivers, one or more communication chips and/or chip sets, and so on. In a more particular example, communications systems 518 can include hardware, firmware and/or software that can be used to establish a Wi-Fi connection, a Bluetooth connection, a cellular connection, an Ethernet connection, and so on.

In some embodiments, memory 520 can include any suitable storage device or devices that can be used to store instructions, values, data, or the like, that can be used, for example, by processor 512 to present content using display 514, to communicate with one or more computing devices 450, and so on. Memory 520 can include any suitable volatile memory, non-volatile memory, storage, or any suitable combination thereof. For example, memory 520 can include RAM, ROM, EEPROM, one or more flash drives, one or more hard disks, one or more solid state drives, one or more optical drives, and so on. In some embodiments, memory 520 can have encoded thereon a server program for controlling operation of server 452. In such embodiments, processor 512 can execute at least a portion of the server program to transmit information and/or content (e.g., data, images, a user interface) to one or more computing devices 450, receive information and/or content from one or more computing devices 450, receive instructions from one or more devices (e.g., a personal computer, a laptop computer, a tablet computer, a smartphone), and so on.

In some embodiments, data source 402 can include a processor 522, one or more inputs 524, one or more communications systems 526, and/or memory 528. In some embodiments, processor 522 can be any suitable hardware processor or combination of processors, such as a CPU, a GPU, and so on. In some embodiments, the one or more inputs 524 are generally configured to acquire data, images, or both, and can include an MRI system. Additionally or alternatively, in some embodiments, one or more inputs 524 can include any suitable hardware, firmware, and/or software for coupling to and/or controlling operations of an MRI system. In some embodiments, one or more portions of the one or more inputs 524 can be removable and/or replaceable.

Note that, although not shown, data source 402 can include any suitable inputs and/or outputs. For example, data source 402 can include input devices and/or sensors that can be used to receive user input, such as a keyboard, a mouse, a touchscreen, a microphone, a trackpad, a trackball, and so on. As another example, data source 402 can include any suitable display devices, such as a computer monitor, a touchscreen, a television, etc., one or more speakers, and so on.

In some embodiments, communications systems 526 can include any suitable hardware, firmware, and/or software for communicating information to computing device 450 (and, in some embodiments, over communication network 454 and/or any other suitable communication networks). For example, communications systems 526 can include one or more transceivers, one or more communication chips and/or chip sets, and so on. In a more particular example, communications systems 526 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 528 can include any suitable storage device or devices that can be used to store instructions, values, data, or the like, that can be used, for example, by processor 522 to control the one or more inputs 524, and/or receive data from the one or more inputs 524; to images from data; present content (e.g., images, a user interface) using a display; communicate with one or more computing devices 450; and so on. Memory 528 can include any suitable volatile memory, non-volatile memory, storage, or any suitable combination thereof. For example, memory 528 can include RAM, ROM, EEPROM, one or more flash drives, one or more hard disks, one or more solid state drives, one or more optical drives, and so on. In some embodiments, memory 528 can have encoded thereon, or otherwise stored therein, a program for controlling operation of data source 402. In such embodiments, processor 522 can execute at least a portion of the program to generate images, transmit information and/or content (e.g., data, images) to one or more computing devices 450, receive information and/or content from one or more computing devices 450, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for generating radiomic feature data from magnetic resonance images and magnetic resonance fingerprinting maps, the method comprising:

(a) accessing with a computer system, magnetic resonance imaging (MRI) data acquired from a subject with an MRI system;

(b) accessing with the computer system, magnetic resonance fingerprinting (MRF) data acquired from the subject, wherein the MRF data comprise quantitative parameter maps;

(c) preprocessing the MRI data and the MRF data with the computer system;

(d) performing an integrated radiomic analysis on the preprocessed MRI data and the preprocessed MRF data with the computer system to generate output as radiomic feature data, wherein the integrated radiomic analysis extracts radiomic features from coregistered MRI and MRF data within regions-of-interest, where the radiomic features comprise at least shape features, first-order statistical features, and second-order statistical features computed from the quantitative parameter maps of the MRF data; and (e) generating a report based on the radiomic feature data using the computer system.

2. The method of claim 1, wherein preprocessing the MRI data and the MRF data comprises:

denoising and bias correcting the MRI data, generating output as denoised MRI data;

segmenting the denoised MRI data and the MRF data, generating output as segmented MRI data and segmented MRF data;

coregistering the segmented MRI data and the segmented MRF data.

3. The method of claim 2, wherein the segmented MRI data are coregistered with the segmented MRF data using one of the quantitative parameter maps contained in the segmented MRF data as a reference.

4. The method of claim 3, wherein the reference comprises a longitudinal relaxation time (T1) map.

5. The method of claim 2, wherein the MRI data comprise multi-contrast MRI data including magnetic resonance images having different contrast weightings.

6. The method of claim 5, wherein one of the different contrast weightings comprises T2-weighted images.

7. The method of claim 6, wherein segmenting the denoised MRI data comprises affinely registering the denoised MRI data to one of the T2-weighted images.

8. The method of claim 1, wherein the radiomic feature data comprise at least one of shape data, first-order statistical feature data, or second-order statistical feature data.

9. The method of claim 8, wherein the shape data comprise at least one of volume or surface area of regions-of-interest in the MRI data and the MRF data.

10. The method of claim 8, wherein the first-order statistical feature data comprise at least one of mean or variance of image values within regions-of-interest in the MRI data and the MRF data.

11. The method of claim 8, wherein the second-order statistical feature data comprise at least one of gray-level co-occurrence matrix-based features, gray-level run length matrix-based features, gray-level size zone matrix-based features, neighborhood gray tone difference matrix-based features, or gray level dependence matrix-based features computed for image values within one or more regions-of-interest in the MRI data and the MRF data.

12. The method of claim 1, wherein generating the report comprises computing statistical features of the radiomic feature data and displaying the statistical features to a user using the computer system.

13. The method of claim 1, wherein preprocessing the MRI data and the MRF data comprises coregistering the MRI data and the MRF data.

14. The method of claim 13, wherein the MRI data and the MRF data are coregistered based on an affine transformation.

15. The method of claim 13, wherein the MRI data comprise T2-weighted images and images with other contrast weightings, wherein the images with other contrast weightings are coregistered to the T2-weighted images.

16. The method of claim 15, wherein the MRF data are coregistered to the MRI data using an affine registration using a maximization of normalized mutual information (NMI).

17. The method of claim 16, wherein the MRF data comprise longitudinal relaxation time (T1) maps and other quantitative parameter maps, wherein the MRF data are coregistered with the MRI data using the T1 maps as a reference for the affine registration using the maximization of NMI.

* * * * *